United States Patent [19]

Morrison et al.

[11] Patent Number: 5,284,643
[45] Date of Patent: Feb. 8, 1994

[54] GALLIUM-CONTAINING ZEOLITE MCM-22

[75] Inventors: Roger A. Morrison, Lambertville, N.J.; Mae K. Rubin, Bala Cynwyd, Pa.

[73] Assignee: Mobil Oil Corp., Fairfax, Va.

[21] Appl. No.: 988,583

[22] Filed: Dec. 10, 1992

[51] Int. Cl.$^5$ .............................................. C01B 33/20
[52] U.S. Cl. .................................... 423/705; 423/326; 423/328.2; 423/329.1; 502/61; 502/64
[58] Field of Search ................ 502/64, 61; 423/328.2, 423/329.1, 704, 705

[56] References Cited

U.S. PATENT DOCUMENTS

| | | | |
|---|---|---|---|
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 5,019,664 | 5/1991 | Del Rossi et al. | 585/419 |
| 5,108,969 | 4/1992 | Del Rossi et al. | 502/66 |
| 5,149,679 | 9/1992 | Price et al. | 502/61 |
| 5,149,894 | 9/1992 | Holtermann et al. | 585/467 |
| 5,192,725 | 3/1993 | Holmgren | 502/64 |
| 5,200,377 | 4/1993 | Zones et al. | 423/704 |
| 5,231,235 | 7/1993 | Kresge et al. | 502/61 |

*Primary Examiner*—Anthony McFarlane
*Attorney, Agent, or Firm*—Alexander J. McKillop; Dennis P. Santini; Edward F. Kenehan, Jr.

[57] ABSTRACT

There is provided a gallium-containing MCM-22 zeolite. There are also provided methods for making this zeolite and processes for using this zeolite as a catalyst for the conversion of organic molecules. Particular conversions are reforming and the dehydrogenation of methylcyclohexane to form toluene.

5 Claims, No Drawings

GALLIUM-CONTAINING ZEOLITE MCM-22

BACKGROUND

This application relates to gallium-containing zeolite MCM-22. This application also relates to methods for making this zeolite and to processes for using this zeolite as a catalyst for converting organic compounds.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, for example an alkali metal or an alkaline earth metal cation. This can be expressed wherein the ratio of the Group IIIA element, e.g., aluminum, to the number of various cations, such as Ca/2, Sr/2, Na, K, or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865; and 4,104,294 describe crystalline silicate of varying alumina and metal content.

Zeolite MCM-22 is described in U.S. Pat. Nos. 4,954,325 and 5,108,969, the entire disclosures of which are expressly incorporated herein by reference.

SUMMARY

There is provided a gallium-containing MCM-22 zeolite having a composition comprising the molar relationship $$X_2O_3:(n)YO_2$$

where n is at least about 10, X is at least one trivalent element, and Y is at least one tetravalent element, wherein X comprises gallium.

There is also provided a method for making a gallium-containing MCM-22 zeolite having a composition comprising the molar relationship $$X_2O_3:(n)YO_2$$

where n is at least about 10, X is at least one trivalent element, and Y is at least one tetravalent element, wherein X comprises gallium, said method comprising preparing a reaction mixture capable of forming said material upon crystallization, said reaction mixture containing sufficient amounts of alkali or alkaline earth metal cations, a source of tetravalent Y oxide, a source of trivalent X oxide comprising a source of gallium oxide, water and hexamethyleneimine, and maintaining said reaction mixture under sufficient crystallization conditions until crystals of said material are formed.

There is also provided a process for converting an organic compound, said process comprising contacting said organic compound under sufficient conversion conditions with a catalyst comprising a gallium-containing MCM-22 zeolite.

EMBODIMENTS

The crystalline material of this invention has a composition involving the molar relationship:

$$X_2O_3:(n)YO_2$$

wherein X is at least one trivalent element comprising gallium, optionally in combination with one or more other trivalent elements, such as aluminum, boron, and/or iron; Y is at least one tetravalent element such as silicon and/or germanium, preferably silicon; and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$$(0.005-0.1)Na_2O(1-4)R:X_2O_3\cdot nYO_2$$

wherein R is an organic moiety. The Na and R components are associated with the material as a result of their presence during crystallization, and are easily removed by post-crystallization methods hereinafter more particularly described.

The crystalline material of the invention is thermally stable and exhibits high surface area (greater than 400 m²/gm) and unusually large sorption capacity when compared to previously described crystal structures having similar X-ray diffraction patterns. As is evident from the above formula, the crystalline material of this invention is synthesized nearly free of Na cations. It can, therefore, be used as a catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In its calcined form, the crystalline material of the invention appears to be made up of a single crystal phase with little or no detectable impurity crystal phases and has an X-ray diffraction pattern which is distinguished from the patterns of other known crystalline materials by the lines listed in Table 1 below:

TABLE 1

| Interplanar d-Spacing (A) | Relative Intensity, I/Io × 100 |
| --- | --- |
| 30.0 ± 2.2 | W-M |
| 22.1 ± 1.3 | W | more specifically by the lines listed in Table 2 below:

TABLE 2

| Interplanar d-Spacing (A) | Relative Intensity, I/Io × 100 |
| --- | --- |
| 30.0 ± 2.2 | W-M |
| 22.1 ± 1.3 | W |
| 3.91 ± 0.07 | M-VS | and yet more specifically by the lines listed in Table 3 below:

TABLE 3

| Interplanar d-Spacing (A) | Relative Intensity, I/Io × 100 |
| --- | --- |
| 30.0 ± 2.2 | W-M |
| 22.1 ± 1.3 | W |
| 6.00 ± 0.10 | W-M |
| 4.06 ± 0.07 | W-S |
| 3.91 ± 0.07 | M-VS |

Most specifically, the calcined crystalline material of the invention has an X-ray diffraction pattern which includes the lines listed in Table 4 below:

TABLE 4

| Interplanar d-Spacing (A) | Relative Intensity, I/Io × 100 |
| --- | --- |
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |

TABLE 4-continued

| Interplanar d-Spacing (A) | Relative Intensity, I/Io × 100 |
| --- | --- |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstrom Units (A), corresponding to the recorded lines, were determined. In Tables 1–4, the relative intensities are given in terms of the symbols W=weak, M=medium, S=strong and VS=very strong. In terms of intensities, these may be generally designated as follows:

$W = 0-20$ $M = 20-40$ $S = 40-60$ $VS = 60-100$

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g., silicon to aluminum, ratio of the particular sample, as well as its degree of thermal treatment.

When used as a catalyst, the crystalline material of the invention should be subjected to thermal treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. while subatmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

The crystalline material of this invention, when employed either as an adsorbent or as a catalyst in an organic compound conversion process should be dehydrated, at least partially. This can be done by heating to a temperature in the range of 200° C. to 595° C. in an atmosphere such as air, nitrogen, etc., and at atmospheric, subatmospheric or superatmospheric pressures for between 30 minutes and 48 hours. Dehydration can also be performed at room temperature merely by placing the silicate in a vacuum, but a longer time is required to obtain a sufficient amount of dehydration.

The present crystalline material can be prepared from a reaction mixture containing sources of alkali or alkaline earth metal (M), e.g., sodium or potassium, cation, an oxide of trivalent element X including gallium, optionally in combination with an oxide of another trivalent element, e.g., aluminum and/or boron, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-80 | 10-60 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5. |

In the present synthesis method, the source of $YO_2$ must be comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method taught in U.S. Pat. No. 4,439,409. If another source of oxide of silicon, e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material of this invention. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the present crystalline material can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the present crystalline material from the above reaction mixture may be hexamethyleneimine which has the following structural formula:

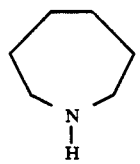

Other organic directing agents which may be used include 1,4-diazacycloheptane, azacyclooctane, aminocyclohexane, aminocycloheptane, aminocyclopentane, N,N,N-trimethyl-1-adamantanammonium ions, and N,N,N-trimethyl-2-adamantanammonium ions. In general, the organic directing agent may be selected from the group consisting of heterocyclic imines, cycloalkyl amines, and adamantane quaternary ammonium ions.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the new crystals is facilitated by the presence of at least 0.01 percent, preferably 0.10 percent and still more preferably 1 percent, seed crystals (based on total weight) of crystalline product.

The crystalline material having the X-ray diffraction patterns of Tables 1-4 passes through an intermediate stage. The material at this intermediate stage has a different X-ray diffraction pattern than those set forth in Tables 1-4. It has further been discovered that this intermediate material is swellable with the use of suitable swelling agents such as cetyltrimethylammonium compounds, e.g., cetyltrimethylammonium hydroxide. However, when this swollen intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance.

The material having the X-ray diffraction pattern of Tables 1-4, when intercepted in the swellable, intermediate state, prior to final calcination, may have the X-ray diffraction pattern shown in Table 5.

TABLE 5

| d(A) | I/I$_o$ |
| --- | --- |
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.10 | w-m |
| 3.95 ± 0.08 | w-vs |
| 3.56 ± 0.06 | w-m |
| 3.43 ± 0.06 | m-vs |
| 3.36 ± 0.05 | w-s |

A particular example of such an as-synthesized, swellable material is the material of Example 1 of the aforementioned U.S. Pat. No. 4,954,325. This material of Example 1 of U.S. Pat. No. 4,954,325 has the X-ray diffraction pattern given in the following Table 6.

TABLE 6

| 2 Theta | d(A) | I/I$_o$ × 100 |
| --- | --- | --- |
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein by reference. The present modifications are discussed hereinafter and include the selection of proper swelling pH and swelling agent.

Upon being swollen with a suitable swelling agent, such as a cetyltrimethylammonium compound, the swollen material may have the X-ray diffraction pattern shown in Table 7.

TABLE 7

| d(A) | I/I$_o$ |
| --- | --- |
| >32.2 | vs |
| 12.41 ± 0.25 | w-s |

TABLE 7-continued

| d(A) | I/I$_o$ |
| --- | --- |
| 3.44 ± 0.07 | w-s |

The X-ray diffraction pattern of this swollen material may have additional lines with a d(A) spacing less than the line at 12.41 ±0.25, but none of said additional lines have an intensity greater than the line at the d(A) spacing of 12.41±0.25 or at 3.44±0.07, whichever is more intense. More particularly, the X-ray diffraction pattern of this swollen material may have the lines shown in the following Table 8.

TABLE 8

| d(A) | I/I$_o$ |
| --- | --- |
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 5 for the unswollen material, but with the possibility of broadening of peaks.

Upon being pillared with a suitable polymeric oxide, such as polymeric silica, the swollen material having the X-ray diffraction pattern shown in Table 7 may be converted into a material having the X-ray diffraction pattern shown in Table 9.

TABLE 9

| d(A) | I/I$_o$ |
| --- | --- |
| >32.2 | vs |
| 12.38 ± 0.25 | w-m |
| 3.42 ± 0.07 | w-m |

The X-ray diffraction pattern of this pillared material may have additional lines with a d(A) spacing less than the line at 12.38 ±0.25, but none of said additional lines have an intensity greater than the line at the d(A) spacing of 12.38±0.25 or 3.42 ±0.07, whichever is more intense. More particularly, the X-ray diffraction pattern of this pillared material may have the lines shown in the following Table 10.

TABLE 10

| d(A) | I/I$_o$ |
| --- | --- |
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 11.

TABLE 11

| 2 Theta | d(A)  | I/I$_o$ × 100 |
|---------|-------|---------------|
| 3.8     | 23.3  | 12            |
| 7.02    | 12.59 | 100           |
| 8.02    | 11.02 | 20            |
| 9.66    | 9.16  | 14            |
| 12.77   | 6.93  | 7             |
| 14.34   | 6.18  | 45            |
| 15.75   | 5.63  | 8             |
| 18.19   | 4.88  | 3             |
| 18.94   | 4.69  | 3             |
| 19.92   | 4.46  | 13 broad      |
| 21.52   | 4.13  | 13 shoulder   |
| 21.94   | 4.05  | 18            |
| 22.55   | 3.94  | 32            |
| 23.58   | 3.77  | 16            |
| 24.99   | 3.56  | 20            |
| 25.94   | 3.43  | 61            |
| 26.73   | 3.33  | 19            |
| 31.60   | 2.831 | 3             |
| 33.41   | 2.682 | 4             |
| 34.62   | 2.591 | 3 broad       |
| 36.36   | 2.471 | 1             |
| 37.81   | 2.379 | 4             |

The X-ray powder pattern shown in Table 11 is similar to that shown in Table 4 except that most of the peaks in Table 11 are much broader than those in Table 4.

As mentioned previously, the calcined material corresponding to the X-ray diffraction pattern of Tables 1-4 is designated MCM-22. For the purposes of the present disclosure, the pillared material corresponding to the X-ray diffraction pattern of Table 9 is designated herein as MCM-36. The swollen material corresponding to the X-ray diffraction pattern of Table 7 is designated herein as the swollen MCM-22 precursor. The as-synthesized material corresponding to the X-ray diffraction pattern of Table 5 is referred to herein, simply, as the MCM-22 precursor.

The layers of the swollen material of this disclosure may have a composition involving the molar relationship:

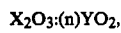

X$_2$O$_3$:(n)YO$_2$, wherein X is at least one trivalent element comprising gallium, optionally in combination with one or more other trivalent elements, such as aluminum, boron, and/or iron; Y is at least one tetravalent element such as silicon and/or germanium, preferably silicon; and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 R$_2$O:X$_2$O$_3$, where R is a monovalent cation or 1/m of a cation of valency m.

The pillared material of the present disclosure adsorbs significant amounts of commonly used test adsorbate materials, i.e., cyclohexane, n-hexane and water. Adsorption capacities for the pillared material, especially the silica pillared material, of the present invention may range at room temperature as follows:

| Adsorbate   | Capacity Wt. Percent |
|-------------|----------------------|
| n-hexane    | 17–40                |
| cyclohexane | 17–40                |
| water       | 10–40                | wherein cyclohexane and n-hexane sorption are measured at 20 Torr and water sorption is measured at 12 Torr.

The swellable material, used to form the swollen material of the present disclosure, may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having a solids content of less than 30 % by weight, e.g., 25 wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 $m^2/g$, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropylorthosilicate, tetramethylorthosilicate and, most preferably, tetraethylorthosilicate. Suitable polymeric silica precursor materials also include quaternary ammonium silicates, e.g., tetramethylammonium silicate (i.e., TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt % for $C_6$ hydrocarbon). The pillared products may possess a basal spacing of at least about 32.2Å and surface areas greater than 500 $m^2/g$.

The swelling and pillaring of MCM-22 precursor in order to form MCM-36 is described in copending U.S. Application Ser. No. 07/811,360, filed Dec. 20, 1991, the entire disclosure of which is expressly incorporated herein by reference.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material of this invention can be used to catalyze a wide variety of chemical conversion processes including many of present commercial/industrial importance. Specific examples of chemical conversion processes which are effectively catalyzed by the crystalline material of this invention, by itself or in combination with one or more other catalytically active substances including other crystalline catalysts, include the following: cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g., methanol, or ethers, e.g., dimethylether, or mixtures thereof to hydrocarbons including aromatics with reaction conditions including a temperature of from about 300° C. to about 550° C., more preferably from about 370° C. to about 500° C., a pressure of from about 0.01 psi to about 2000 psi, more preferably from about 0.1 psi to about 500 psi, and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating isoalkanes, e.g., isobutane, with olefins, e.g., 2-butene, with reaction conditions including a temperature of from about −25° C. to about 400° C., e.g., from about 75° C. to about 200° C., a pressure of from below atmospheric to about 5000 psig, e.g., from about atmospheric to about 1000 psig, a weight hourly space velocity based on olefin of from about 0.01 to about 100, e.g., from about 0.1 to about 20, and a mole ratio of total isoalkane to total olefin of from about 1:2 to about 100:1, e.g., from about 3:1 to about 30:1; alkylating aromatic hydrocarbons, e.g., benzene and alkylbenzenes, in the presence of an alkylating agent, e.g., olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1; reacting olefins, e.g., isobutene or isopentene, with alcohols, e.g., methanol, to produce ethers with reaction conditions including a temperature of from about 20° C. to about 200° C., a total system pressure of from about 1 to about 200 atmospheres, an alcohol to olefin mole ratio of from about 0.1 to about 5 and a weight hourly space velocity of from 0.1 to about 200; converting light olefins, e.g., having 2 to 7 carbon atoms, to alcohol(s), ether(s) or mixtures thereof by reacting said light olefins with water under reaction conditions including a temperature from about 50° C. to about 300° C., a total pressure of at least about 5 atmospheres; and a mole ratio of water to total olefin of from about 0.1 to about 30; and transferring hydrogen from paraffins to olefins with reaction conditions including a temperature from about −25° C. to about 400° C., e.g., from about 75° C. to about 200° C., a pressure from below atmospheric to about 5000 psig, e.g., from about atmospheric to about 1000 psig, a mole ratio of total paraffin to total olefin of from about 1:2 to about 500:1, e.g., from about 5:1 to about 100:1; and a weight hourly space velocity based on olefin of from about 0.01 to about 100, e.g., from about 0.05 to about 5.

A particular example of a hydrocarbon conversion process, which involves the use of a catalyst comprising the present gallium-containing MCM-22, is a reforming process. A reforming process involving the use of an MCM-22 catalyst is described in U.S. Pat. No. 5,019,664, the entire disclosure of which is expressly incorporated herein by reference.

The feedstream to a reforming process may contain at least 20%, and more preferably at least 50%, by weight of aliphatic hydrocarbon(s) containing 1 to 12 carbon atoms. The hydrocarbon(s) can be straight chain, open chain, or cyclic, and can be saturated or unsaturated. Some contemplated hydrocarbons are ethane, propane, propylene, n-butane, n-butenes, isobutane, isobutene, straight chain, branched chain, and cyclic pentanes, pentenes, hexanes, hexenes, heptanes, heptenes, octanes, octenes, nonanes, nonenes, decanes, undecanes, decenes, undecenes, dodecanes, and dodecenes. A particularly useful hydrocarbon feedstock herein is a raffinate from a hydrocarbon mixture which has had aromatic removed therefrom by a solvent extraction treatment. Examples of such solvent extraction treatments are described in *Kirk-Othmer Encyclopedia of Chemical Technology*, 9, 706–709 (1980). One such hydrocarbon feedstock is a Udex raffinate, a typical composition of which is as follows:

| Component | Wt. % |
|---|---|
| $C_5$ | 6.20 |
| $C_5=$ | 0.19 |
| $C_6$ | 45.80 |
| $C_6=$ | 8.49 |
| $C_7$ | 27.93 |
| $C_8$'s | 3.56 |
| Benzene | 0.39 |
| Toluene | 3.85 |
| EB | 0.34 |
| Xylene | 0.39 |
| $C_9$ + Aromatics | 1.18 |

A reforming catalyst may comprise a Group VIII metal component. The expression "Group VIII metal species" as used herein contemplates the metal per se or a compound thereof. The Group VIII noble metals and their compounds, e.g., platinum, palladium, iridium, rhenium, and rhodium, or combinations thereof can be used. The preferred metals are platinum and palladium; and of these, platinum is the most preferred. The Group VIII metal component can be physically and/or chemically associated with the zeolite and/or any binder or matrix material with which the zeolite may be composited. For example, the Group VIII metal species can be impregnated into the zeolite crystals after they are formed or the metal can be included in the reaction mixture from which this zeolite is formed. The Group VIII metal can also be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride, and any of various compounds containing a platinum amine complex. The amount of Group VIII metal present in the catalyst can vary from about 0.01 to 5.0 wt. %, preferably about 0.1 to about 2.0 wt. %, and most preferably about 0.2 to about 1.0 wt. %.

The conversion of paraffin to aromatic hydrocarbon in accordance with a reforming process may be conducted so that a feed containing a relatively high percentage, e.g., at least 20 wt. %, preferably at least 50 wt. %, of $C_2$–$C_{12}$ aliphatic hydrocarbon(s) is contacted with the catalyst in a reaction zone such as, for example, a fixed or fluid bed of the catalyst composition under effective conversion conditions. In a typical embodiment of the reformimg process, the feedstream is introduced into the reaction zone at a temperature within the range of from about 600° F. to about 1400° F., preferably from about 800° F. to 1000° F., a pressure within the range of from about atmospheric to about 400 psig, preferably from about 50 to about 250 psig, and a liquid hourly space velocity (LHSV) of from about 0.1 $hr^{-1}$ to about 100 $hr^{-1}$, preferably from about 0.5 $hr^{-1}$ to about 5 $hr^{-1}$.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane and/or n-hexane, they were Equilibrium Adsorption values determined as follows:

A weighed sample of the calcined adsorbant was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. The new synthetic material of this invention always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of the present crystalline material.

EXAMPLE 1

Catalyst Preparation

MCM-22 preparations were carried out hydrothermally using the precipiated silicas, HiSil or Ultrasil, hexamethyleneimine, and sodium hydroxide. The sources of alumina were either aluminum sulfate or sodium aluminate. Ferric ammonium sulfate, gallium oxide, and boric acid were used as sources for the iron, gallium, and boron. The gallium preparations were also seeded with conventional MCM-22. The mixtures were crystallized at 300° F. in stainless steel autoclaves with 200–300 rpm agitation. The hydrogen form was obtained by calcining in air for 16 hours and then contacting with $NH_4Cl$ solution for a total of 5 one-hour contacts at 180° F. Details of the synthesis mixtures and chemical analysis of the final exchanged materials are listed in Table 12.

TABLE 12

Synthesis Conditions and Chemical Analysis of Metal-MCM-22 Catalysts

| Metal | Al— | Fe— | Ga— | Ga—Al— | Ga—B— |
|---|---|---|---|---|---|
| Synthesis Conditions | | | | | |
| $SiO_2$/$Al_2O_3$ | — | 138 | — | 200 | — |
| $SiO_2$/$Fe_2O_3$ | — | 19 | — | — | — |
| $SiO_2$/$B_2O_3$ | — | — | — | — | 16 |
| $SiO_2$/$Ga_2O_3$ | — | — | 12 | 15 | 59 |
| Silica source | — | Ultrasil | Hi Sil | Ultrasil | Ultrasil |
| Seeds, % | — | — | 3 | 3 | 3 |
| Crystallization, Days, 300° F. | — | 28 | 16 | 10 | 10 |

TABLE 12-continued

Synthesis Conditions and Chemical Analysis of Metal-MCM-22 Catalysts

| Metal | Al— | Fe— | Ga— | Ga—Al— | Ga—B— |
|---|---|---|---|---|---|
| Finished Catalysts-Chemical Analysis, Wt. % | | | | | |
| $SiO_2$ | — | 78.5 | 63.9 | 72.2 | 82.4 |
| $Al_2O_3$ | — | 1.1 | 0.34 | 0.79 | 0.15 |
| Ga | — | — | 11.2 | 10.1 | 2.8 |
| B | — | — | — | — | 0.61 |
| Fe | — | 8.7 | — | — | — |
| Na | — | 0.01 | 0.24 | 0.04 | 0.04 |
| % $Al_2O_3$ Binder | 35 | — | — | — | — |
| $SiO_2/Al_2O_3$ | 26 | 121 | 320 | 156 | 915 |
| $SiO_2/Ga_2O_3$ | — | — | 13 | 17 | 66 |
| $SiO_2/B_2O_3$ | — | — | — | — | 49 |
| $SiO_2/Fe_2O_3$ | — | 17 | — | — | — |
| $SiO_2/(Al + Fe)_2O_3$ | — | 15 | — | — | — |
| $SiO_2/(Al + Ga)_2O_3$ | — | — | 13 | 15 | — |
| $SiO_2/(Al + ga + B)_2O_3$ | — | — | — | — | 27 |
| Mesh Size | 20 × 60 | 30 × 60 | 20 × 60 | 30 × 60 | 30 × 60 |

In the Examples which follow, catalytic evaluations were made of the materials prepared in accordance with Example 1. These catalytic evaluations were performed in a glass reactor with 0.5 grams of catalyst. The standard pretreat was 30 minutes in dry flowing air at 1000° F. Regeneration between experiments was at the same conditions for 15 minutes or until the original catalyst color was restored. The analyses were performed using on-line sampling onto a 6 foot × ⅛ inch OV-101 packed GC column. With this analysis the propane and propylene usually elute together. Thus, the data reflect only propane, whereas both components may be present. An approximation to the propylene content may sometimes be inferred from the olefin content of the $C_2$'s and $C_4$'s.

For reference, additional information is included in the Tables from previously run experiments. This includes an Al-containing MCM-22, Pt-Re/$Al_2O_3$, [Ga]-ZSM-11, and [Ga]-zeolite beta in methylcyclohexane dehydrogenation and naphtha aromatization, and ZSM-20 in dodecane cracking. To minimize repetition in the report, the MCM-22 materials are referred to by Y component as "Al", "Fe", "Ga?", "Ga-Al", "Ga-B" (see Table 12 for more complete catalyst descriptions.) A detailed presentation of data corresponding to Examples considered to be less relevant has been omitted.

EXAMPLE 2

Long Chain Paraffin Cracking (Dodecane)

Long chain paraffin cracking patterns show some interesting characteristics relative to ZSM-20 and [Al]-MCM-22, as shown in the Table below:

| | | MCM-22 | | | | |
|---|---|---|---|---|---|---|
| Catalyst | ZSM-20 | Al | Ga | Ga-Al | Ga-B | Fe |
| Temp., °F. | 600 | 475 | 650 | 500 | 550 | 650 |
| Wt. % Conversion | 58 | 33 | 25 | 40 | 38 | 45 |
| n-$C_6$/Methyl | 0.1 | 0.6 | 0.1 | 0.1 | 0.1 | 0.5 |
| Pentanes Selectivities, Wt. % | | | | | | |
| $C_1$-$C_4$ | 35 | 49 | 36 | 38 | 44 | 57 |
| $C_5$-$C_{11}$ | 63 | 47 | 60 | 56 | 51 | 42 |

More detailed information regarding the reactions involving the Ga-MCM-22 (Ga), H-MCM-22 (Al), and H-ZSM-22 (ZSM-20) catalysts is given in Table 13.

TABLE 13

Dodecane Cracking over Ga-MCM-22, Al-MCM-22, and ZSM-20

| Temperature, °F. | 650.00 | 475.00 | 600.00 |
|---|---|---|---|
| RXN Time (min.) | 20.00 | 20.00 | 20.00 |
| Pressure, ATM | 1.00 | 1.00 | 1.00 |
| $H_2$/HC | 5.10 | 5.10 | 5.10 |
| WHSV | 3.00 | 3.00 | 3.00 |
| Catalyst Type | Ga-MCM-22 | H-MCM-22 | H-ZSM-20 |
| $SiO_2/Al_2O_3$ | 400/1 | 26 | 8.3/1 |
| Mesh | 20 × 60 | 20 × 60 | 40 × 60 |
| Binder | none | 35% $Al_2O_3$ | none |
| Product Dist., wt. % | | | |
| $C_1$ | 0.23 | 0.00 | 0.00 |
| $C_2 + C_2=$ | 0.62 | 0.03 | 0.10 |
| $C_3 + C_3=$ | 2.13 | 1.61 | 3.51 |
| Iso-$C_4$ | 4.45 | 10.58 | 13.52 |
| N—$C_4$ | 1.58 | 2.26 | 2.44 |
| $C_4=$ | 0.00 | 1.81 | 0.78 |
| Iso-$C_5$ | 4.77 | 2.78 | 12.73 |
| N—$C_5$ | 0.32 | 0.34 | 0.73 |
| $C_5=$ | 0.16 | 2.34 | 0.51 |
| Cyclo-$C_5$ | 0.37 | 0.76 | 0.00 |
| 2,3-DM—$C_4$ | 0.00 | 0.60 | 1.25 |
| 2-M—$C_5$ | 1.47 | 0.30 | 4.94 |
| 3-M—$C_5$ | 1.27 | 0.06 | 2.95 |
| N—$C_6$ | 0.17 | 0.21 | 0.47 |
| $C_6=$ | 0.00 | 0.36 | 0.14 |
| M-Cyclo-$C_5$ | 0.00 | 0.23 | 0.79 |
| Benzene | 0.00 | 0.04 | 0.04 |
| Cyclo-$C_6$ | 0.00 | 0.13 | 0.00 |
| $C_7$ Par. + OL. | 3.27 | 2.91 | 7.14 |
| $C_8$ + Par. + OL. | 3.39 | 4.56 | 4.48 |
| Iso-$C_{12}$ | 1.05 | 1.38 | 1.24 |
| Dodecane | 74.76 | 66.68 | 42.21 |
| $C_{13}$+ (All) | 0.00 | 0.07 | 0.00 |
| Wt. % Conv., Total | 25.24 | 32.97 | 57.79 |
| Selectivities | | | |
| $C_1$-$C_4$ | 35.68 | 49.40 | 35.24 |
| $C_5$-$C_{11}$ | 60.14 | 47.16 | 62.55 |

The three Ga catalysts show characteristics of 12-ring zeolites, e.g., low n-paraffin/isoparaffin selectivity and less light gas vs. gasoline range products. Thus, in long chain paraffin cracking, the substitution of Ga for Al leads to changes in reactivity which are characteristic of 12-ring pore systems rather than the large 10-ring character of the parent MCM-22. The Fe material has low activity.

EXAMPLE 3

Paraffin Isomerization/Cracking (n-Hexane)

In general, paraffin isomerization selectivity tends to increase with zeolite pore size. Thus, 3-dimensional 12-ring zeolites have isomerization selectivities of >30%, whereas 10-rings and less have values <25%. Below is a summary of isomerization selectivities including zeolite beta from previous experiments.

| Catalyst | Beta | MCM-22 | | | | | | |
|---|---|---|---|---|---|---|---|---|
| | | Al | Ga | Ga-Al | | Ga-B | | Fe |
| Temp., °F. | 550 | 600 | 650 | 600 | 650 | 650 | 700 | 700 |
| Wt. % Conversion | 28 | 13 | 7 | 9 | 21 | 9 | 16 | 4 |
| Isom. Sel. | 35 | 25 | 57 | 67 | 45 | 58 | 32 | 48 |

The results above show that substitution of gallium for aluminum provides improved isomerization selectivity of MCM-22 with values more characteristic of 12-ring zeolite. However, metals may independently catalyze this reaction by facilitating olefinic intermediate formation. Thus, the observed higher isomerization selectivity is not necessarily related to structure although the results are consistent with a 12-ring reaction character.

EXAMPLE 4

Reforming Activity/Dehydrogenation (Methylcyclohexane)

Another unique property of Ga-MCM-22 materials (no Pt) occurs in methylcyclohexane dehydrogenation. For the Ga materials, the aromatic selectivity, primarily toluene, is 90–96% at 100% conversion. This high selectivity is comparable to Pt-Re/Al$_2$O$_3$ reforming catalyst which has a selectivity of 93% at the same reaction conditions. Data are given in Tables 14, 15, and 16.

TABLE 14

Methylcyclohexane Dehydrogenation over Ga-MCM-22 vs. Reforming Catalyst

| Temperature, °F. | 1000.00 | 1000.00 |
|---|---|---|
| RXN Time (min.) | 20.00 | 20.00 |
| Pressure, ATM | 1.00 | 1.00 |
| H$_2$/HC | 3.10 | 3.10 |
| WHSV | 3.10 | 0.75 |
| Catalyst Type | Ga-MCM-22 | Pt-Re/Al$_2$O$_3$ |
| SiO$_2$/Al$_2$O$_3$ | 400/1 | — |
| Metal, wt. % | Gallium = 11.2 | Rhenium = 3.5 |
| | | Platinum = 3.5 |
| Mesh | 20 × 60 | 20 × 60 |
| Binder | none | Al$_2$O$_3$ |
| Product Dist., wt. % | | |
| C$_1$ | 1.39 | 0.53 |
| C$_2$= | 0.00 | 2.29 |
| C$_2$ | 1.33 | 1.53 |
| C$_3$ | 0.45 | 1.30 |
| Iso-C$_4$ | 0.67 | 0.28 |
| N—C$_4$ | 0.00 | 0.57 |
| Iso-C$_5$ | 0.13 | 0.13 |
| N—C$_5$ | 0.00 | 0.08 |
| C$_5$= | 0.08 | 0.02 |
| Cyclo-C$_5$ | 0.16 | 0.03 |
| Benzene | 4.92 | 5.97 |
| C$_7$ Par. + OL. | 0.39 | 0.15 |
| M-Cyclo-C$_6$ | 0.00 | 0.00 |
| Toluene | 3.27 89.49 | 85.04 |
| C$_8$ AR. | 0.99 | 1.70 |
| C$_9$ AR. | 0.00 | 0.16 |
| Naphthalenes | 0.00 | 0.18 |
| C$_{11}$ + AR. | 0.00 | 0.04 |
| Wt. % Conv., Total | 100.00 | 100.00 |
| Selectivities | | |
| C$_1$-C$_4$ | 3.84 | 6.50 |
| C$_5$ + P + O | 0.76 | 0.41 |
| Toluene | 89.49 | 85.04 |
| C$_8$ + AR. | 0.99 | 2.08 |
| Total AR. | 95.40 | 93.09 |

TABLE 15

Methylcyclohexane Conversion over MCM-22 Made With Various Metals

| Temperature, °F. | 1000.00 | 1000.00 | 1000.00 | 1000.00 | 1000.00 |
|---|---|---|---|---|---|
| RXN Time (min.) | 20.00 | 20.00 | 20.00 | 20.00 | 20.00 |
| Pressure, ATM | 1.00 | 1.00 | 1.00 | 1.00 | 1.00 |
| H$_2$/HC | 3.10 | 3.10 | 3.10 | 3.10 | 3.10 |
| WHSV | 3.10 | 3.10 | 3.10 | 3.10 | 3.10 |
| Catalyst Type | Ga-MCM-22 | Ga-B-MCM-22 | Ga-Al-MCM-22 | Fe-MCM-22 | Al-MCM-22 |
| SiO$_2$/Al$_2$O$_3$ | 400/1 | 1100/1 | 138/1 | ~150/1 | 24/1 |
| Mesh | 20 × 60 | 30 × 60 | 30 × 60 | 30 × 60 | 40 × 60 |
| Product Dist., wt. % | | | | | |
| C$_1$ | 1.39 | 2.50 | 2.71 | 2.31 | 5.52 |
| C$_2$= | 0.00 | 0.56 | 0.00 | 0.00 | 6.92 |
| C$_2$ | 1.33 | 1.19 | 1.67 | 1.10 | 4.09 |
| C$_3$ | 0.45 | 2.17 | 0.95 | 1.75 | 21.12 |
| Iso-C$_4$ | 0.67 | 1.20 | 0.42 | 0.68 | 9.77 |
| N—C$_4$ | 0.00 | 0.78 | 0.27 | 0.54 | 3.31 |
| C$_4$= | 0.00 | 0.00 | 0.00 | 0.78 | 2.77 |
| Iso-C$_5$ | 0.13 | 0.26 | 0.00 | 0.23 | 2.02 |
| N—C$_5$ | 0.00 | 0.00 | 0.00 | 0.00 | 0.41 |
| C$_5$= | 0.08 | 0.00 | 0.00 | 0.17 | 0.50 |
| Cyclo-C$_5$ | 0.16 | 0.00 | 0.00 | 0.39 | 0.21 |
| 2-M—C$_5$ | 0.00 | 0.00 | 0.00 | 0.00 | 0.10 |
| 3-M—C$_5$ | 0.00 | 0.00 | 0.00 | 0.00 | 0.10 |
| M-Cyclo-C$_5$ | 0.00 | 0.00 | 0.00 | 0.09 | 0.05 |
| Benzene | 4.92 | 9.94 | 9.04 | 4.55 | 5.92 |
| C$_7$ Par. + OL. | 0.39 | 0.00 | 0.00 | 2.44 | 0.00 |
| M-Cyclo-C$_6$ | 0.00 | 0.00 | 0.00 | 68.08 | 0.00 |
| Toluene | 89.49 | 78.56 | 80.93 | 14.33 | 17.88 |
| C$_8$ AR. | 0.99 | 2.34 | 2.13 | 1.22 | 10.11 |
| C$_9$ AR. | 0.00 | 0.49 | 0.29 | 0.31 | 3.63 |
| C$_{10}$ AR. | 0.00 | 0.00 | 0.00 | 0.09 | 0.83 |
| Naphthalenes | 0.00 | 0.00 | 1.59 | 0.94 | 4.75 |
| Wt. % Conv., Total | 100.00 | 100.00 | 100.00 | 31.92 | 100.00 |
| Selectivities | | | | | |
| C$_1$-C$_4$ | 3.84 | 8.41 | 6.03 | 22.41 | 53.51 |
| C$_5$ + P + O | 0.76 | 0.26 | 0.00 | 10.40 | 3.39 |
| Toluene | 89.49 | 78.56 | 80.93 | 44.88 | 17.88 |
| C$_8$ + AR. | 0.99 | 2.83 | 4.01 | 8.04 | 19.31 |
| Total AR. | 95.40 | 91.33 | 93.97 | 67.19 | 43.11 |

TABLE 16

METHYLCYCLOHEXANE DEHYDROGENATION OVER VARIOUS Ga-ZEOLITES

| Temperature, °F. | 1000.00 | 1000.00 | 1000.00 |
|---|---|---|---|
| RXN Time (min.) | 20.00 | 20.00 | 20.00 |
| Pressure, ATM | 1.00 | 1.00 | 1.00 |
| H$_2$/HC | 3.10 | 0.00 | 0.00 |
| WHSV | 3.10 | 1.40 | 1.40 |
| Catalyst Type | Ga-MCM-22 | Ga-ZSM-11 | Ga-Beta |
| SiO$_2$/Al$_2$O$_3$ | 400/1 | 383 ppm Al$_2$O$_3$ | 183:1 |
| Wt. % Ga | 11.2 | 3.5 | 5.1 |
| Mesh | 20 × 60 | 20 × 40 | 20 × 40 |
| Binder | none | none | none |
| Product Dist., wt. % | | | |
| C$_1$ | 1.39 | 6.16 | 6.46 |
| C$_2$= | 0.00 | 1.25 | 1.76 |
| C$_2$ | 1.33 | 2.92 | 5.99 |
| C$_3$ | 0.45 | 6.85 | 6.43 |
| Iso-C$_4$ | 0.67 | 0.08 | 0.85 |
| N—C$_4$ | 0.00 | 0.32 | 1.35 |
| C$_4$= | 0.00 | 0.00 | 0.17 |
| Iso-C$_5$ | 0.13 | 0.00 | 0.05 |
| N—C$_5$ | 0.00 | 0.00 | 0.09 |
| C$_5$= | 0.08 | 0.00 | 0.01 |
| Cyclo-C$_5$ | 0.16 | 0.00 | 0.00 |
| Benzene | 4.92 | 18.38 | 18.23 |
| C$_7$ Par. + OL. | 0.39 | 0.02 | 0.00 |
| M-Cyclo-C$_6$ | 0.00 | 0.00 | 0.00 |

TABLE 16-continued

METHYLCYCLOHEXANE DEHYDROGENATION OVER VARIOUS Ga-ZEOLITES

| Toluene | 89.49 | 49.32 | 39.46 |
|---|---|---|---|
| $C_8$ AR. | 0.99 | 8.89 | 9.44 |
| $C_9$ AR. | 0.00 | 1.24 | 1.22 |
| $C_{10}$ AR. | 0.00 | 0.39 | 0.12 |
| Naphthalenes | 0.00 | 3.50 | 6.58 |
| $C_{11}$ + AR. | 0.00 | 0.67 | 1.76 |
| Wt. % Conv., Total | 100.00 | 100.00 | 100.00 |
| Selectivities | | | |
| $C_1$-$C_4$ | 3.84 | 17.58 | 23.01 |
| Toluene | 89.49 | 49.32 | 39.46 |
| $C_8$ + AR. | 0.99 | 14.69 | 19.13 |
| Total Aromatics | 95.40 | 82.40 | 76.83 |

The data in Table 16 show the dehydrogenation selectivity is unique relative to two other low Al, Ga-containing zeolites (ZSM-11 and zeolite beta). Their maximum selectivity for aromatics is 82%, but they also exhibit characteristics of aromatics formed by extensive cracking followed by recombination of the fragments into a wide distribution of aromatics. This type of distribution is largely absent from the Ga materials although the Ga-Al catalyst does show small aspects of this chemistry, probably due to its higher Al content. Thus, the lack of significant cracked products and continuum of aromatic products supports a primarily dehydrogenation mechanism for Ga materials. In addition, the dehydrogenation activity level of the Ga materials is high, i.e., the Ga-Al material gives 100% methylcyclohexane conversion at ~850° F.

EXAMPLE 5

Aromatic Isomerization (m-Xylene)

There are two significant features of xylene isomerization. First, as with toluene disproportionation, the Ga-B material has more activity than the others. It gives close to xylene equilibrium at ~900° F. vs. 950°–1000° F. for the other metal catalysts. Second, the disproportionation selectivity, which increases with increasing pore size, is higher for the metal-containing MCM-22 materials (25–45 vs. 15% for [Al]-MCM-22, at similar o-xylene approach to equilibrium). This suggests that the space available at the Al siting in [Ga]-MCM-22 is larger than in [Al]-MCM-22 and again confirms a shift to 12-ring reaction character for these materials.

EXAMPLE 6

Naphtha Reforming

Because of the dehydrogenation activity/selectivity of the Ga catalysts, it was of interest to determine if the activity extended to real naphthas. Thus, these materials were evaluated on a naphthene-rich hydrotreated $C_5$-330° F. Arab Naphtha, Table 17, and an n-paraffin-rich $C_5$-360° F. Naphtha. For reference, comparable runs were made on a Pt-Re/$Al_2O_3$ reforming catalyst. (Octanes and volumetric recoveries were calculated from the product distributions.)

TABLE 17

Conversion of Hydrocracked Arab Naphtha over Reforming Catalyst and GA-MCM-22

| Catalyst Type | Pt-Re/$Al_2O_3$ | Ga-MCM-22 |
|---|---|---|
| Temperature, °F. | 1000 | 1000 |
| Pressure, psig | 1 | 1 |
| WHSV | 2.9 | 2.9 |
| $H_2$/HC | 3/1 | 3/1 |
| Time on stream, min. | 20 | 20 |

TABLE 17-continued

Conversion of Hydrocracked Arab Naphtha over Reforming Catalyst and GA-MCM-22

| Product Dist., wt. % | | | ~75—>300° F. |
|---|---|---|---|
| $C_1$ | 1.2 | 0.6 | Hydrocracked |
| $C_2$ + $C_2$= | 2.0 | 1.2 | Arab Naphtha |
| $C_3$ + $C_3$= | 2.5 | 2.1 | |
| Iso-$C_4$ | 0.8 | 0.9 | 0.3 |
| N—$C_4$ | 2.1 | 1.3 | 0.6 |
| $C_4$= | 1.4 | 1.9 | — |
| Iso-$C_5$ | 2.8 | 2.9 | 2.8 |
| N—$C_5$ | 2.2 | 2.3 | 1.7 |
| $C_5$= | 1.7 | 1.4 | — |
| 2,2 Dm-$C_4$ | 0.3 | 0.2 | — |
| Cyclo-$C_5$ | 0.2 | 0.4 | 0.3 |
| 2,3 DM-$C_4$ | 0.7 | 0.4 | 0.4 |
| 2-M-$C_5$ | 2.7 | 3.0 | 3.4 |
| 3-M-$C_5$ | 1.7 | 1.9 | 2.1 |
| N—$C_6$ | 1.4 | 2.4 | 2.4 |
| $C_6$= | 0.8 | 0.5 | — |
| M-Cyclo-$C_5$ | 1.7 | 2.7 | 3.3 |
| Benzene | 4.7 | 2.3 | 1.1 |
| Cyclo-$C_6$ | — | — | 1.0 |
| $C_7$'s | 10.6 | 13.4 | 19.4 |
| N—$C_7$ | 1.4 | 2.4 | 2.3 |
| Toluene | 12.6 | 9.2 | 4.7 |
| $C_8$'s | 7.2 | 9.4 | 15.3 |
| N—$C_8$ | 1.5 | 2.5 | 3.9 |
| $C_8$ AR. | 17.7 | 14.9 | — |
| $C_9$ + Par. | 2.6 | 5.0 | 34.9 |
| $C_9$ AR. | 10.7 | 10.6 | — |
| $C_{10}$ AR. | 4.0 | 3.0 | 100.0 |
| Naphthalenes | 0.5 | 0.0 | |
| M-Naphthalenes | 0.3 | 0.1 | |
| Wt. % Conv. total | 57.3 | 44.5 | |
| To $C_1$-$C_4$ | 9.1 | 7.0 | |
| To aromatics | 44.7 | 34.5 | |
| Selectivity, wt. % | | | |
| $C_1$-$C_4$ made | 15.8 | 15.7 | |
| Aromatics made | 78.0 | 77.7 | |

From the foregoing data one can conclude that Ga-MCM-22 is:

(1) effective for dehydrogenation similar to Pt-Re/$Al_2O_3$ reforming catalyst.

(2) different from other MCM-22 preps like Al or Fe.

(3) different from other Ga-containing zeolites which have more cracking activity and so less dehydrogenation selectivity.

(4) different from Al-MCM-22 for cracking/hydrocracking because it has 12-ring character vs. the 10-ring character of Al-MCM-22. A practical result of this change is more gasoline range product.

Particular data which support the above conclusions are provided in Tables 13–17.

The results in Table 14 show Ga-MCM-22 is as effective as, if not slightly better than, standard reforming catalyst for dehydrogenation of methylcyclohexane to aromatics. It has the benefit of not requiring an expensive metal such as Pt or Re. Further, the catalyst is effective on charge stocks such as found in refineries as seen in Table 17 where reforming of an Arab Naphtha over reforming catalyst vs. Ga-MCM-22 is shown.

The data in Table 17 show that on real charge stocks, Ga-MCM-22 can make aromatics (high octane gasoline) with the same selectivity (78%) as reforming catalyst, but again with no Pt or Re.

The uniqueness of Ga-MCM-22 compared to other preps of MCM-22 which contain metals in combination with Ga and without Ga is demonstrated in Table 15.

The data in Table 15 show that Ga by itself (expect for impurity Al) or in combination with B or higher levels of Al are equally selective for aromatics (>90%), but that either Fe or conventional Al-MCM-22 are not effective and yield considerable cracked ($C_1$–$C_4$) products. Large amounts of cracked products are typical of zeolites in general.

As suggested in Table 16, Ga-MCM-22 is unique among Ga-containing zeolites including both 10- and 12-membered ring pore opening examples, i.e., ZSM-11 and Beta.

The results in Table 16 show Ga-MCM-22 is unique in aromatic selectivity compared to either size zeolite. Further, the Ga-MCM-22 has even less cracked product than the Ga-ZSM-11 which has much less $A_nO_3$ Without being bound by any theory, it is theorized that this may be due to a separation of the Ga and Al in Ga-MCM-22 which makes it unique, but here would not appear to be a way to prove this theory, other than deductively from the reaction data.

As suggested in Table 13, when Ga-MCM-22 is used for acid reactions, such as cracking, paraffin/olefin alkylation, etc., it behaves more like a 12-ring zeolite than a 10-ring zeolite as does conventional Al-MCM-22.

The data in Table 13 show that Ga-MCM-22 makes more gasoline range hydrocarbon, similar to the 12-ring ZSM-20, than does the conventional Al-MCM-22.

What is claimed is:

1. A gallium-containing MCM-22 zeolite having a composition comprising the molar relationship $$X_2O_3:(n)YO_2$$

where n is at least about 10, X is at least one trivalent element, and Y is at least one tetravalent element, wherein X comprises gallium.

2. A gallium-containing MCM-22 zeolite according to claim 1, wherein X consists of gallium.

3. A gallium-containing MCM-22 zeolite according to claim 1, wherein X comprises gallium and aluminum.

4. A gallium-containing MCM-22 zeolite according to claim 1, wherein X comprises gallium and boron.

5. A method for making a gallium-containing MCM-22 zeolite having a composition comprising the molar relationship $$X_2O_3:(n)YO_2$$

where n is at least about 10, X is at least one trivalent element, and Y is at least one tetravalent element, wherein X comprises gallium, said method comprising preparing a reaction mixture capable of forming said material upon crystallization, said reaction mixture containing sufficient amounts of alkali or alkaline earth metal cations, a source of tetravalent Y oxide, a source of trivalent Y oxide comprising a source of gallium oxide, water and hexamethyleneimine, and maintaining said reaction mixture under sufficient crystallization conditions until crystals of said material are formed.

* * * * *